(12) United States Patent
Millikin

(10) Patent No.: US 10,899,536 B2
(45) Date of Patent: Jan. 26, 2021

(54) METHOD FOR CANNABINOID DELIVERY INTO BEVERAGES

(71) Applicant: Rory Chesley Patrick Millikin, Kelowna (CA)

(72) Inventor: Rory Chesley Patrick Millikin, Kelowna (CA)

(73) Assignee: Drive Foods Corp, Westminster, CA (US)

( * ) Notice: Subject to any disclaimer, the term of this patent is extended or adjusted under 35 U.S.C. 154(b) by 28 days.

(21) Appl. No.: 16/744,050

(22) Filed: Jan. 15, 2020

(65) Prior Publication Data

US 2020/0377290 A1 Dec. 3, 2020

Related U.S. Application Data

(60) Provisional application No. 62/853,668, filed on May 28, 2019.

(51) Int. Cl.
| | | |
|---|---|---|
| *B65D 85/804* | (2006.01) | |
| *A23F 5/26* | (2006.01) | |
| *A61K 36/18* | (2006.01) | |
| *A23L 33/10* | (2016.01) | |
| *A61K 36/185* | (2006.01) | |
| *A23L 33/105* | (2016.01) | |

(52) U.S. Cl.
CPC .......... *B65D 85/8043* (2013.01); *A23F 5/267* (2013.01); *A23L 33/105* (2016.08); *A61K 36/185* (2013.01); *A23V 2002/00* (2013.01); *A61K 2236/331* (2013.01)

(58) Field of Classification Search
CPC .............. B65D 85/8043; B65D 85/804; B65D 85/8046; A23F 5/267; A61K 36/185; A61K 2236/331; A23L 33/105
See application file for complete search history.

(56) References Cited

U.S. PATENT DOCUMENTS

| | | | |
|---|---|---|---|
| 2014/0106036 A1* | 4/2014 | Cardoso ................ | B65B 29/022 426/115 |
| 2014/0161940 A1* | 6/2014 | Aviles ................ | B65D 81/3233 426/115 |
| 2015/0352044 A1* | 12/2015 | Benson ................. | A61J 1/1443 206/205 |
| 2016/0310443 A1* | 10/2016 | Reillo ..................... | A23F 3/405 |
| 2017/0000744 A1* | 1/2017 | Kaufman ............. | A61K 31/352 |
| 2017/0274028 A1* | 9/2017 | Kennedy .............. | A61K 36/185 |
| 2018/0255801 A1* | 9/2018 | Victor ...................... | A23F 3/34 |
| 2018/0263954 A1* | 9/2018 | Renwick .............. | A61K 31/352 |
| 2019/0291946 A1* | 9/2019 | Tuttle ................. | B65D 85/8043 |
| 2019/0308804 A1* | 10/2019 | Kaiserman ......... | B65D 85/8043 |

\* cited by examiner

*Primary Examiner* — Ericson M Lachica
(74) *Attorney, Agent, or Firm* — Christopher Pilling

(57) ABSTRACT

In hot beverage *cannabis* related products, such as single use coffee systems as well as other coffee systems, the cannabinoids are not being infused into the beverages, such as coffee, during the brewing process. To solve this problem, a cannabinoid delivery system is provided. The cannabinoid delivery system includes various systems and methods of positioning cannabinoids and/or *cannabis* plant matter in locations and forms such that the cannabinoids are properly infused into the beverages.

6 Claims, 9 Drawing Sheets

METHOD FOR CANNABINOID DELIVERY INTO BEVERAGES

CROSS-REFERENCE TO RELATED APPLICATIONS

The present invention is a continuation in part application to U.S. Nonprovisional application Ser. No. 16/600,345, filed Oct. 11, 2019, entitled "IMPROVED METHOD FOR CANNABIONOID DELIVERY INTO BEVERAGES", which is a continuation in part application to U.S. Nonprovisional application Ser. No. 16/449,338, filed Jun. 21, 2019, entitled "IMPROVED METHOD FOR CANNABIONOID DELIVERY INTO BEVERAGES" now U.S. Pat. No. 10,485,373 issued Nov. 26, 2019, which is a continuation in part application to United States Nonprovisonal Application Ser. No. 16/388,821 filed Apr. 18, 2019 entitled "IMPROVED METHOD FOR EXTRACTING CANNABINOIDS FOR IMPROVED BIOAVALABLITY" and the present application claims priority to United Sates Provisional Application Ser. No. 62/853,668 filed on May 28, 2019 entitled "IMPROVED METHOD FOR CBD/CANNABINOID DELIVERY INTO BEVERAGES", the disclosures of which are hereby incorporated in their entirety at least by reference.

BACKGROUND OF THE INVENTION

1. Field of the Invention

The present invention generally relates to *cannabis*, and more particular an improved system and method for cannabinoid delivery into beverages, such as coffee and tea.

2. Description of Related Art

*Cannabis* as a health supplement has been practiced for over 1,000 years. Traditionally *cannabis* is heated to release cannabinoids, primary tetrahydrocannabinol (THC) and cannabidiol (CBD). It is well known that cannabinoids offer many benefits to users, and there are a variety of methods to make cannabinoids available to the user. Recently, there has been a trend to enrich cannabinoids into beverages, such as coffee and tea. Consequently, the present invention provides an improved system and method for cannabinoid delivery into beverages.

BRIEF SUMMARY OF THE INVENTION

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

X TBD after claims are finalized.

The foregoing has outlined rather broadly the more pertinent and important features of the present disclosure so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present disclosure. It should be realized by those skilled in the art that such equivalent structures do not depart from the spirit and scope of the invention as set forth in the appended claims.

BRIEF DESCRIPTION OF THE SEVERAL VIEWS OF THE DRAWINGS

Other features and advantages of the present invention will become apparent when the following detailed description is read in conjunction with the accompanying drawings, in which.

DETAILED DESCRIPTION OF THE PREFERRED EMBODIMENT

Figure 1:
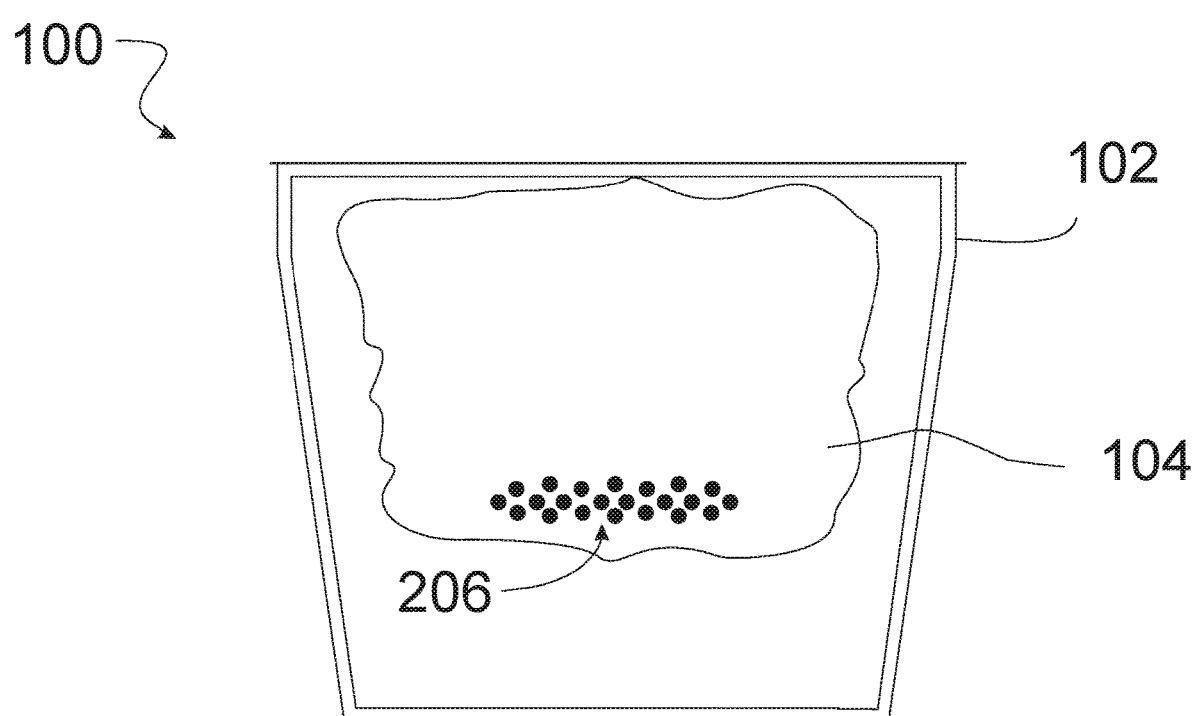
FIG. 1 is a sectional view of a single use coffee filter with the present invention according to an embodiment of the present invention.

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein to specifically provide an improved system and method for cannabinoid delivery into beverages.

For the purpose of this disclosure, the word "a" is defined to mean "at least one." The word "*cannabis*" is defined to mean "any species of the *cannabis* genus of flowing plants including *Cannabis sativa, Cannabis indica, Cannabis ruderalis,* and hemp." The word "*cannabis* plant matter" is defined to mean "any portion, cannabinoid, terpene, phytonutrient, or other compound, either natural, artificial, or synthetic, derived or extracted from a *cannabis* plant or *cannabis* plant DNA." The word "beverage mix" is defined to mean "any ground or powdered beverage flavor, substance, etc. configured to be mixed into water to create a flavored beverage." The terminology includes the words above specifically mentioned, derivatives thereof, and words of similar import.

Recognition of a Problem

As well documented, *cannabis* plant matter is desirable for the cannabinoids that the plant matter contains. The cannabinoids include CBD, THC, as well as other desirable cannabinoids. As companies attempt to offer various means to intake these desirable cannabinoids, one method is through coffee products.

There are many coffee cannabinoid containing products on the market today, and these products claim to have from 5 mg of CBD to 65 mg CBD prior to the brewing process. Testing was performed on 10 of these products to determine the cannabinoid levels infused into the beverage after brewing. Testing protocols were established and applied to each test. The testing was performed with standard coffee machines found in the marketplace using standard coffee filters or single use coffee systems for each test, as indicated by each product's directions. For each test, 8 oz of water was used. After brewing, 10 ml of the brewed coffee from each test was extracted, secured in a vial, then coded and sent for testing at a leading cannabinoid testing facility, Cannalysis Labs in California. The results were conclusive, not a single vial tested had any detectable CBD in the brewed beverage. Since CBD has no intoxicating effects associated with its intake, the consumers of these products are likely unaware that the cannabinoids, in this case CBD, are not reaching the brewed product.

Solution to the Problem

The applicants have concluded that the cannabinoids are not able to penetrate the standard coffee filters or the filters present in the single use coffee systems. Alternatively, the cannabinoids are not being infused into the beverage during the brewing process. Thus, the following disclosure describes various embodiments to solve this problem.

FIG. 1 is a sectional view of a single use coffee containment system 100 according to an embodiment of the present invention. Referring now to FIG. 1, the single use coffee containment system comprises a hollow housing 102 configured to hold a coffee filter bag 104 containing ground coffee (not shown) as well known in the art. In one embodiment, a predetermined amount of ground *cannabis* plant matter 206 at a predetermined size is added to the coffee filter bag 104. The coffee filter bag is constructed of a filter material, such as a mesh, screen, or permeable paper at a predetermined filter size. The predetermined size of the coffee filter bag is smaller than the particle size of the ground coffee, such that the ground coffee is retained in the coffee filter bag during the brewing process. In one embodiment, the predetermined size of the *cannabis* plant matter is smaller than the predetermined size of the coffee filter bag, such that the ground *cannabis* plant matter passes through the coffee filter bag.

During use, the housing of the single use coffee containment system is pierced in both the top surface and the bottom surface of the housing while hot pressurized water passes through the single use coffee containment system into a cup, herein "beverage," positioned below the single use coffee system (not shown) as well known in the art. Thus, after brewing, the beverage would contain a coffee and *cannabis* plant matter (cannabinoid) combination.

Typically, coffee filter are made up of filaments approximately 20 micrometers wide enabling particles to pass through that are less than approximately 15 to 20 micrometers, preferably 10 to 15 micrometers or less. Thus, in one embodiment, the predetermined size of the *cannabis* plant matter is less than 10 micrometers.

In some embodiments, the hollow housing of the system is the filter, such that an additional filter (or filter bag) is not required. This may be referred to the hollow housing having an integrated filter. In this embodiment, the system may be single-use or reusable, wherein the material selection may vary depending on its usage as well known in the art.

Figure 2:
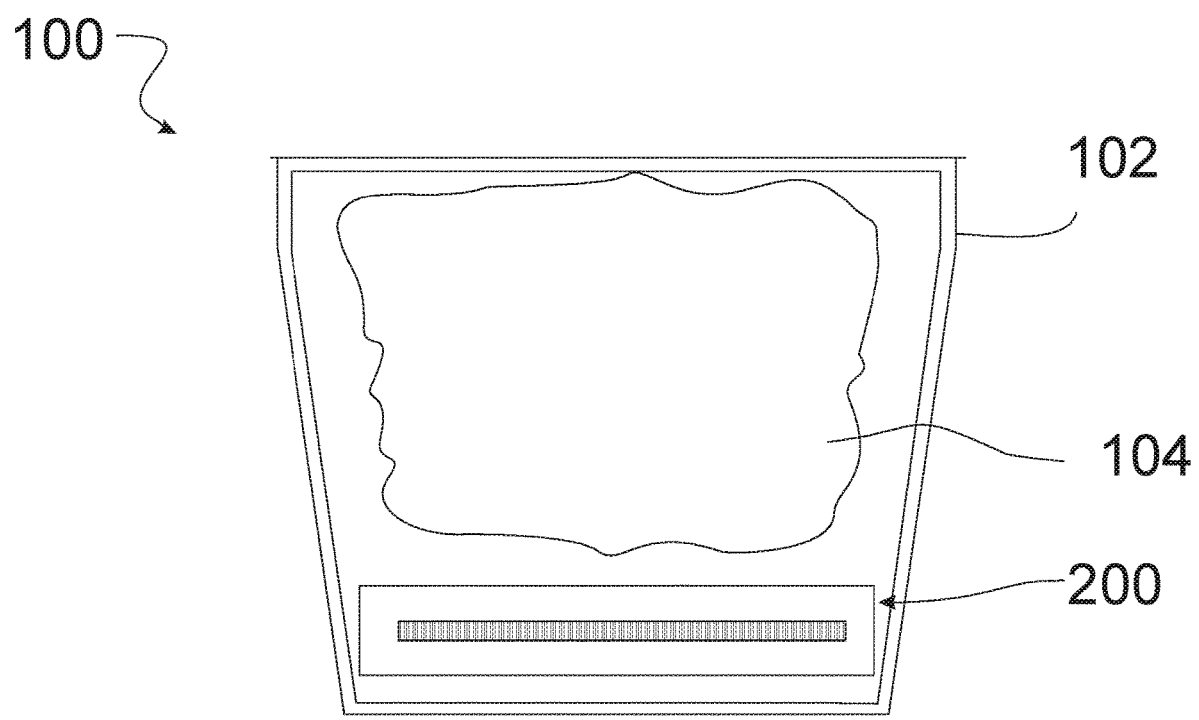
FIG. 2 is a sectional front view of a cannabinoid delivery system in a single use coffee containment system according to an embodiment of the present invention.
Figure 3:
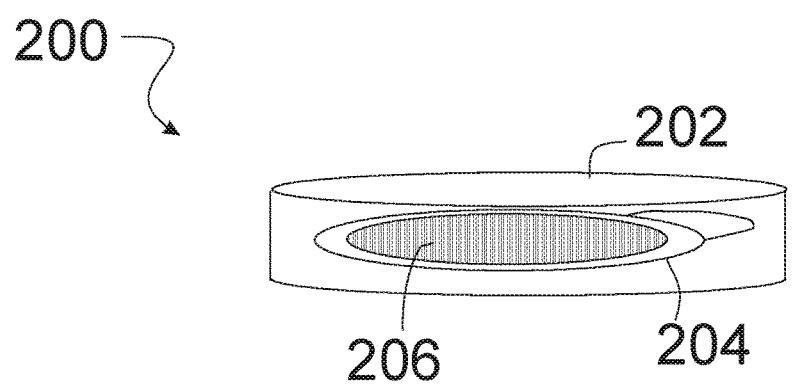
FIG. 3 is a perspective view of a cannabinoid delivery system according to an embodiment of the present invention.

FIG. 2 is a sectional front view of a cannabinoid delivery system 200 in a single use coffee containment system, while FIG. 3 is a perspective view of the cannabinoid delivery system 200. Referring now to FIGS. 2-3, an additional solution to the aforementioned problem is provided. In this embodiment, a cannabinoid delivery system 200 is positioned below the coffee filter bag 104 in the hollow housing 102 of the single use coffee containment system 100. In one embodiment, the cannabinoid delivery system 200 comprises a porous containment element 202 containing a filter pod 204 having a predetermined amount of *cannabis* plant matter 206 wherein the predetermined amount of *cannabis* plant matter contains a specific dosage of cannabinoids. The predetermined amount *cannabis* plant matter may be provided in several forms, which will be discussed below. The porous containment element acts as a protective containment element. In one embodiment, the porous containment element is cylindrically shaped, comprised of a hard food grade material. In one embodiment, the porous containment element comprises pores larger than the openings, filaments, or filter elements of the filter pod.

In one embodiment, the predetermined amount of *cannabis* plant matter is ground *cannabis* plant matter comprised of nanoparticles. The method to reduce the *cannabis* plant matter to nano size is detailed in Applicant's parent application Ser. No. 16/388,821. In one embodiment, the nanoparticles are less than or equal to 120 nanometers. In another embodiment, the nanoparticles are less than 1,000 nanometers. In some embodiments, the nanoparticles are compacted to retain groups of particles larger than the predetermined size of the individual particles. In some embodiments, the nanoparticles are compacted into a dissolvable tablet.

In one embodiment, the predetermined amount of *cannabis* plant matter is comprised in a sublingual strip, wherein the sublingual strip dissolves when the hot pressurized water passes through the filter pod, enabling the cannabinoid containing *cannabis* plant matter to be mixed in the beverage. In some embodiments, extracted cannabinoids are used, including but not limited to cannabinoids in MCT oil, or other lipids. In another embodiment, the *cannabis* plant matter are encapsulated nanoparticles configured to be water soluble, as taught in Applicant's co-pending application Ser. No. 16/439,706 hereby incorporated by reference.

It should be understood, that the form of the *cannabis* plant material depends on the filter pod selected. In one embodiment, the filter pod is a mesh, screen, or paper barrier comprising filter material having a size larger than the individual particle size of the *cannabis* plant matter. In this embodiment, the compacted particles prevent the individual particles from exiting the filter pod prior to the brewing process. In another embodiment, the filter pod is made from a dissolvable material, such that the hot pressurized water dissolves the filter pod enabling the contained *cannabis* plant matter to be mixed with the beverage during the brewing process.

Figure 8A:
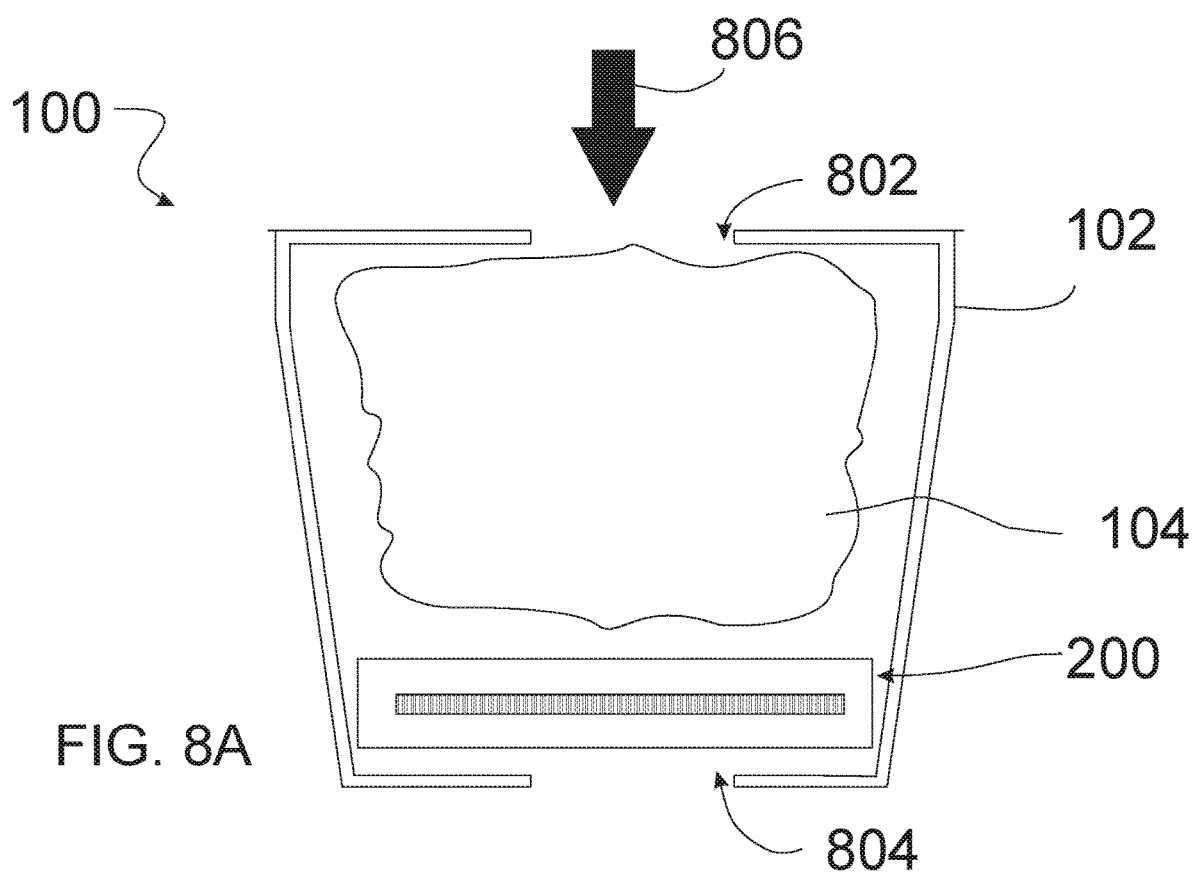
FIGS. 8A-B illustrate the single use coffee filter with the present invention in use according to an embodiment of the present invention.
Figure 8B:
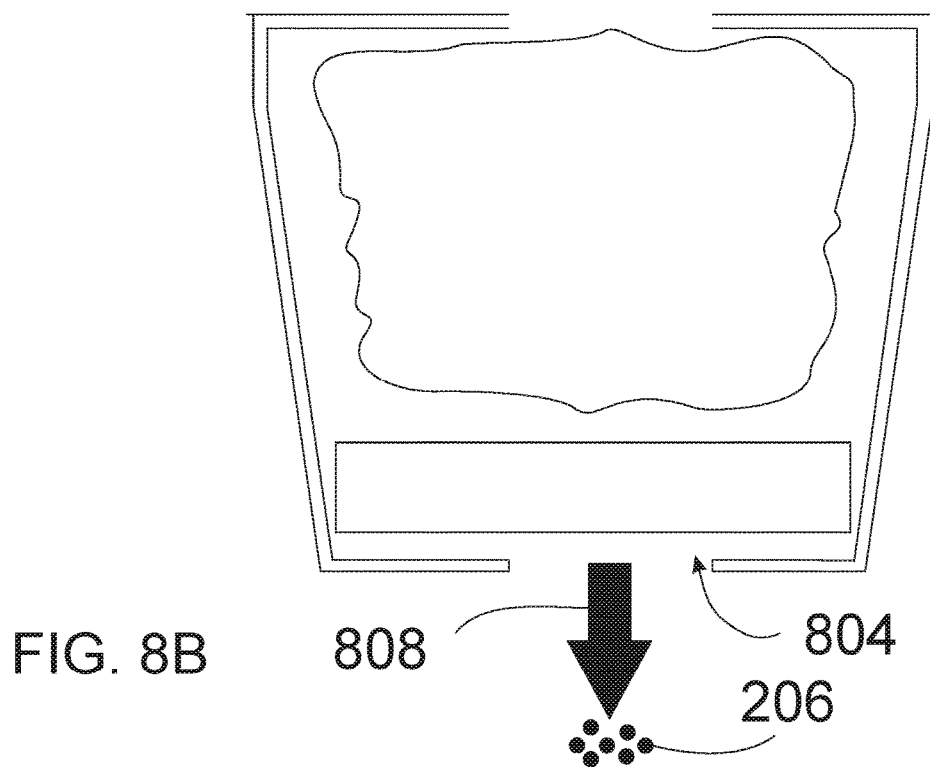

Best seen in FIGS. 8A-B, during use, as previously mentioned, the housing of the single use coffee containment system is pierced in both the top surface 802 and the bottom surface 804 of the housing while hot pressurized water enters the housing 806, through the coffee filter bag, then through the single use coffee containment system, then finally the hot pressurized water exits 808 of the bottom of the housing wherein the hot pressurized water contains extracted coffee and the *cannabis* plant matter 206. The combination is collected in a beverage for consumption as well known in the art, enabling the user to intake the benefits of the cannabinoids.

Figure 4:
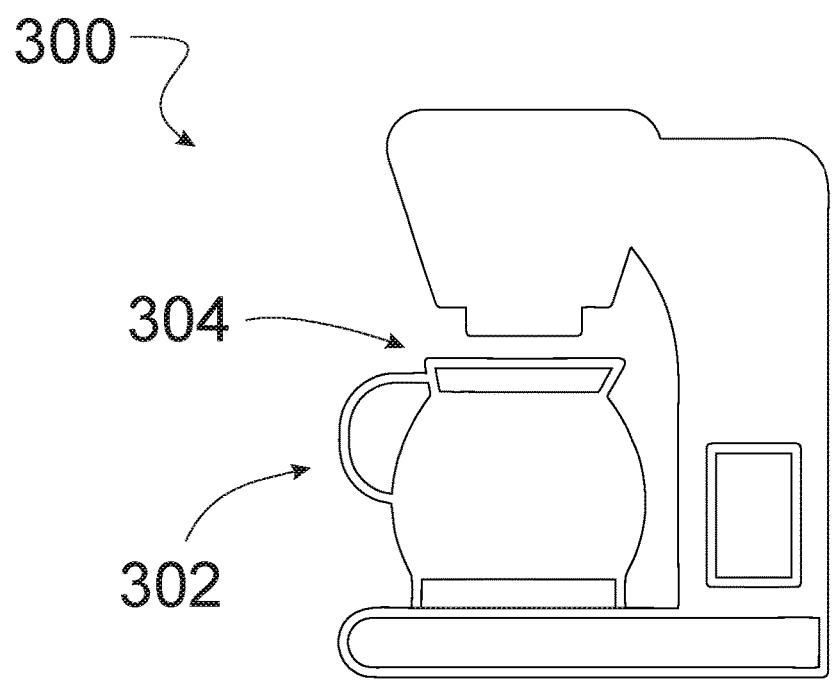
FIG. 4 is a side view of a coffee machine and coffee pot having a cannabinoid delivery system installed in a compartment positioned in the lid of the coffee pot according to an embodiment of the present invention.
Figure 5:
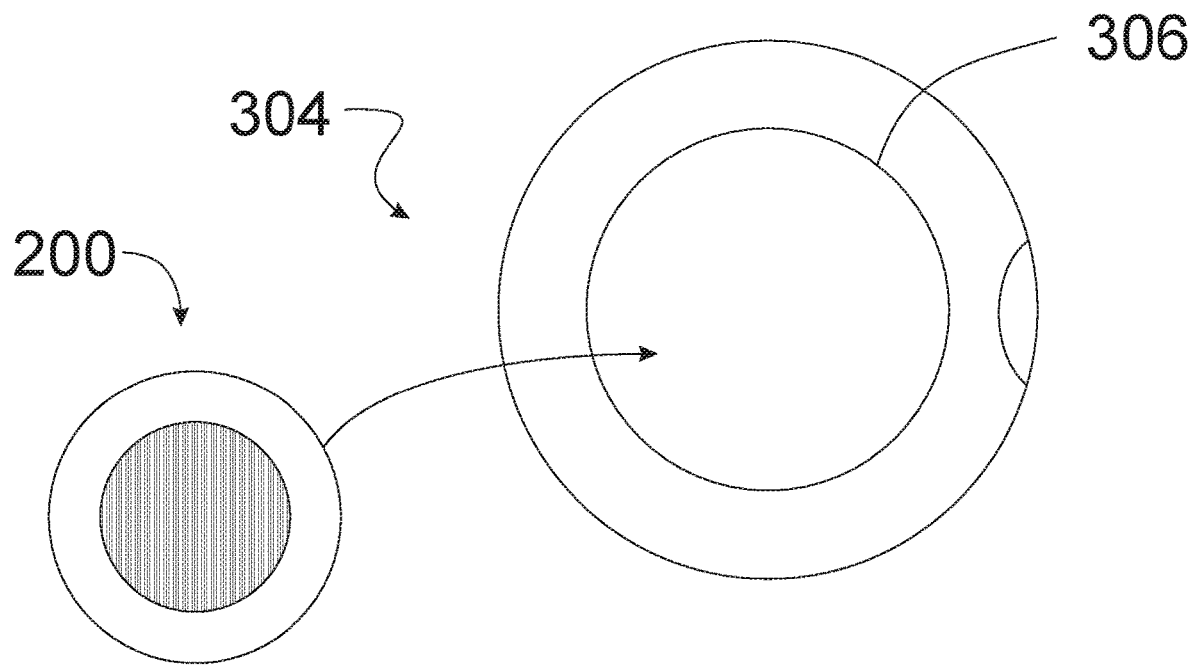
FIG. 5 is a top view of the lid of the coffee pot according to an embodiment of the present invention.

FIG. 4 is a side view of a coffee machine 300 and coffee pot 302 having a cannabinoid delivery system installed in a compartment positioned in the lid of the coffee pot. FIG. 5 is a top view of the lid 304 of the coffee pot. Referring now to FIGS. 4-5, the embodiment disclosed is an alternative to single use coffee systems. In this embodiment, the user simply opens the dedicated compartment 306 in the lid 304 of the coffee pot 302, places the cannabinoid delivery system 200 into the compartment, closes the lid, and finally starts the brewing process. The *cannabis* delivery system may include arrangements and variations to each component as previously discussed. In addition to the previously discussed embodiments, in another embodiment, the user is instructed to shake the cannabinoid delivery system, breaking up the compacted nanoparticles prior to placing the *cannabis* delivery system into the compartment. During the brewing process, hot water is directed from the coffee machine, extracting coffee flavor from the ground coffee placed in the coffee machine as well known in the art. This hot water passes through the compartment, wherein the *cannabis* plant matter is then mixed with the beverage. In one embodiment, coffee machine 300 is a drip coffee machine.

Figure 6:
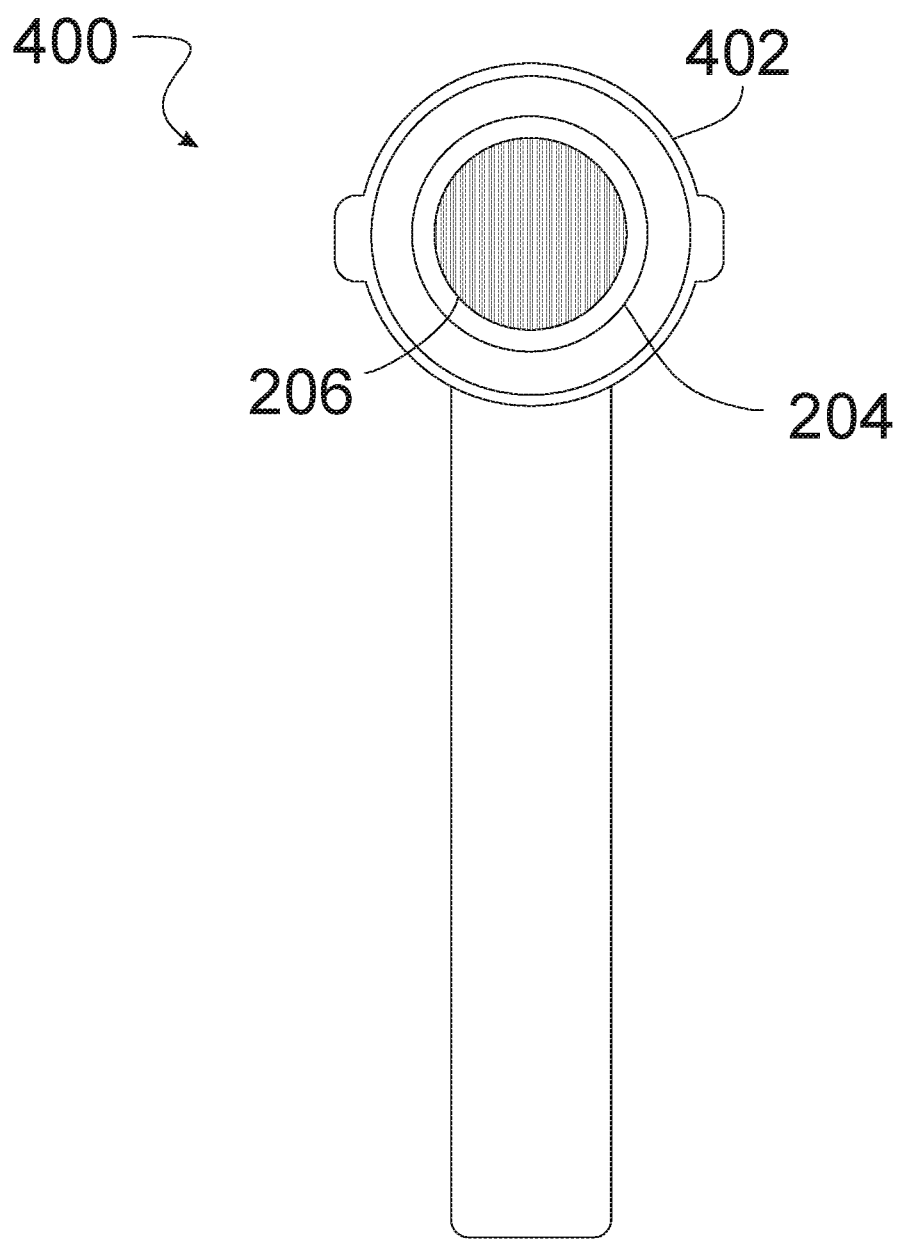
FIG. 6 is a top view of an espresso coffee portafilter having a cannabinoid delivery system installed within the basket according to an embodiment of the present invention.

FIG. 6 is a top view of an espresso coffee portafilter 400 having filter pod 204 installed within the basket 402 according to an embodiment of the present invention. Referring now to FIG. 6, in this embodiment, the *cannabis* delivery system includes the filter pod 204 containing *cannabis* plant matter 206. In some embodiments, the porous containment element is not provided. In other embodiments, the porous containment element may be provided. Although, the porous containment element is thin and small, due to the limited space in the basket 402, ideally, just the filter pod is inserted during use. In one embodiment, the porous containment element is approximately 1.25 inches in diameter and 0.1 inches thick. During use, a user loads a *cannabis* delivery system into the basket 402 of the espresso coffee portafilter 400 along with finely ground coffee as well known in the art. Then the user connects the espresso coffee portafilter and operates the espresso machine (not shown) as normal. During the brewing process, the hot pressurized water extracts the coffee into the beverage and the *cannabis* plant matter is mixed into the coffee beverage. The *cannabis* plant matter may be in any form as previously discussed.

Figure 7:
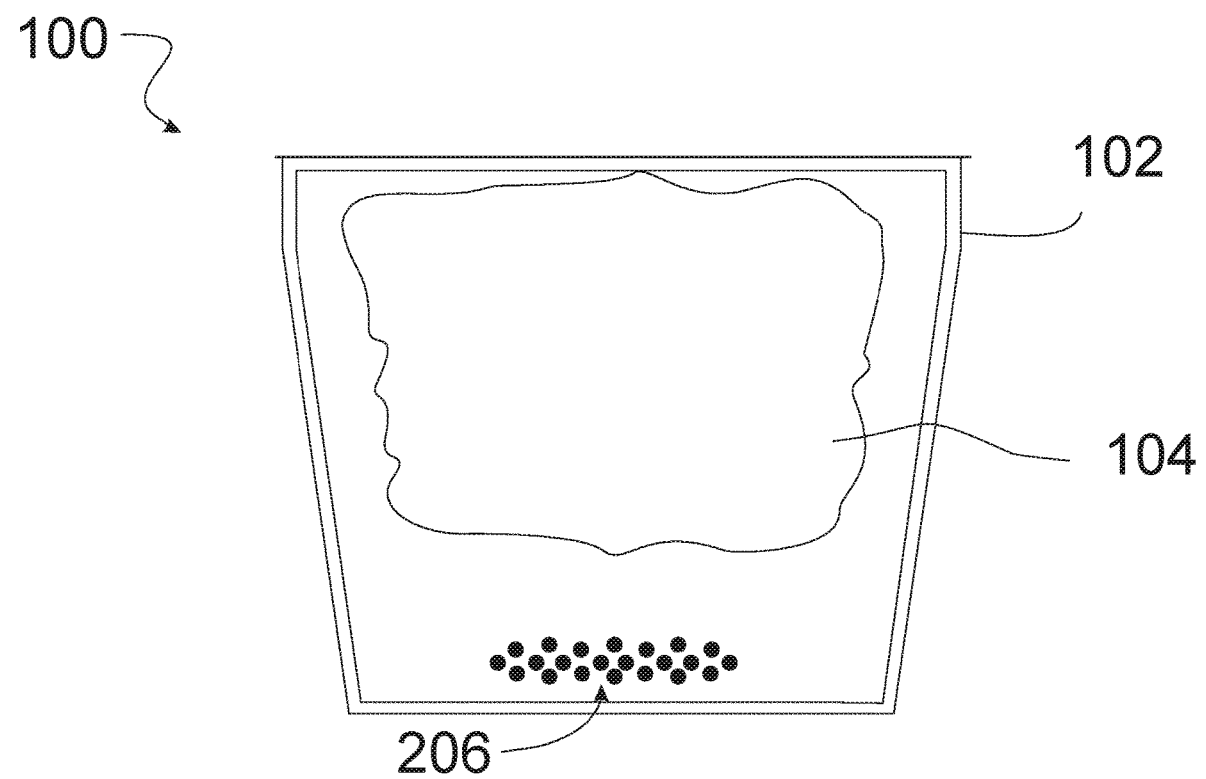
FIG. 7 is a sectional view of a single use coffee filter with the present invention according to an embodiment of the present invention.

Referring now to FIG. 7, in some embodiments, the *cannabis* plant matter may be added to the bottom portion of the hollow housing of the single use coffee containment system, i.e. without the cannabinoid delivery system. Advantageously, special preparation of the *cannabis* plant matter is not required, providing an easy solution to the problem. In this embodiment, the *cannabis* plant matter may be in any form as previously discussed. As sediment is undesirable in beverages, the encapsulated nanoparticles are one of the preferred forms, however, any form previously discussed may be selected.

A particular advantage of the *cannabis* delivery system is that it provides premeasured dosages of various cannabinoids that offer a means to track usage and accountability. In one embodiment, each *cannabis* delivery system is vacuum sealed and packaged individually, to prevent containments and to ensure proper shelf life and handling. In some embodiments, identifying information, including but not limited to barcodes, RFID, insignia, numbers, text, or any other identifying information may be provided on each *cannabis* delivery system. In this way, each *cannabis* delivery system may be tracked and accounted for. In some embodiments, each *cannabis* delivery system may be dispensed from a dispensing machine (not shown) to aid in the tracking and accountability of each *cannabis* delivery system.

Figure 9A:
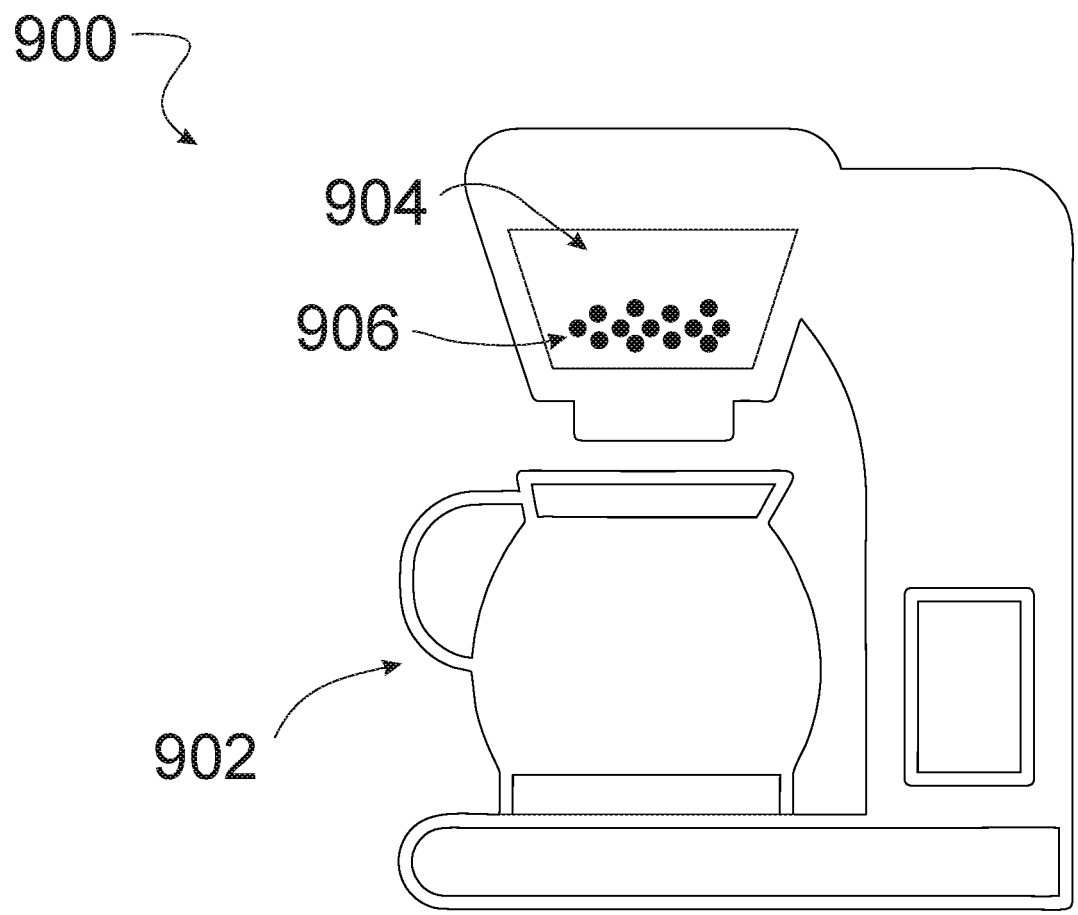
FIG. 9A is a side view of a coffee machine and coffee pot having a cannabinoid delivery system installed in a coffee filter according to an embodiment of the present invention.
Figure 9B:
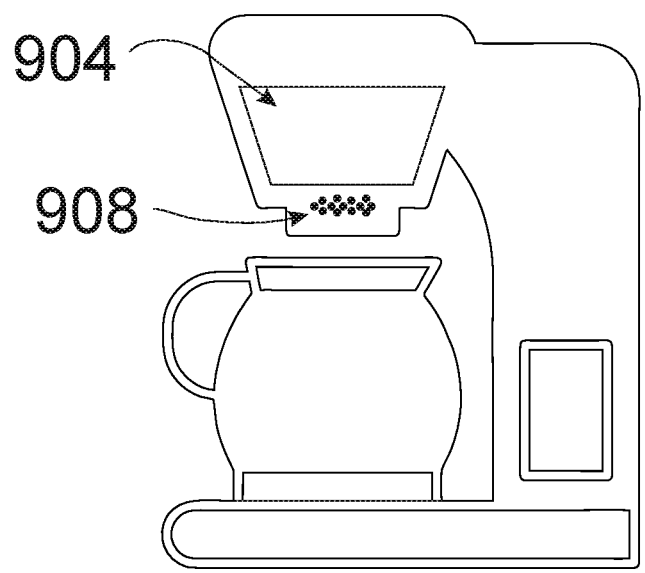
FIG. 9B is a side view of a coffee machine and coffee pot having a cannabinoid delivery system installed under the coffee filter according to an embodiment of the present invention; and, FIGS. 10A-D are sectional views of alternate cannabinoid delivery system illustrating various divider element configurations according to embodiments of the present invention.

FIG. 9A is a side view of a coffee machine 900 and coffee pot 902 having a cannabinoid delivery system installed in a coffee filter 904 according to an embodiment of the present invention. This is an alternative option to the embodiment disclosed in FIG. 4. The coffee machine includes coffee filter 904 having a filter size, wherein the coffee filter is configured to retain ground coffee as well known in the art. In this embodiment, *cannabis* plant matter 906 is positioned in the coffee filter, wherein the wherein the *cannabis* plant matter is smaller than the filter size. As previously defined, the *cannabis* plant matter may be any portion, cannabinoid, terpene, phytonutrient, or other compound, natural, artificial, or synthetic, derived or extracted from a *cannabis* plant or *cannabis* plant DNA. In some embodiments, the *cannabis* plant matter is ground *cannabis*. In other embodiments, the ground coffee grounds are soaked in *cannabis* oil or *cannabis* distillates. In other embodiments, the *cannabis* plant matter is a *cannabis* cannabinoid isolate, such as CBD isolate. The embodiment illustrated in FIG. 9B, is similar to previously discussed, however in this embodiment, the *cannabis* plant matter 908 is positioned below the coffee filter. In some embodiments, the *cannabis* plant matter may be positioned above the coffee filter. In any of the embodiments discussed, the *cannabis* plant matter may be positioned in a filter pod, similar to the previously discussed embodiments.

Figure 10A:
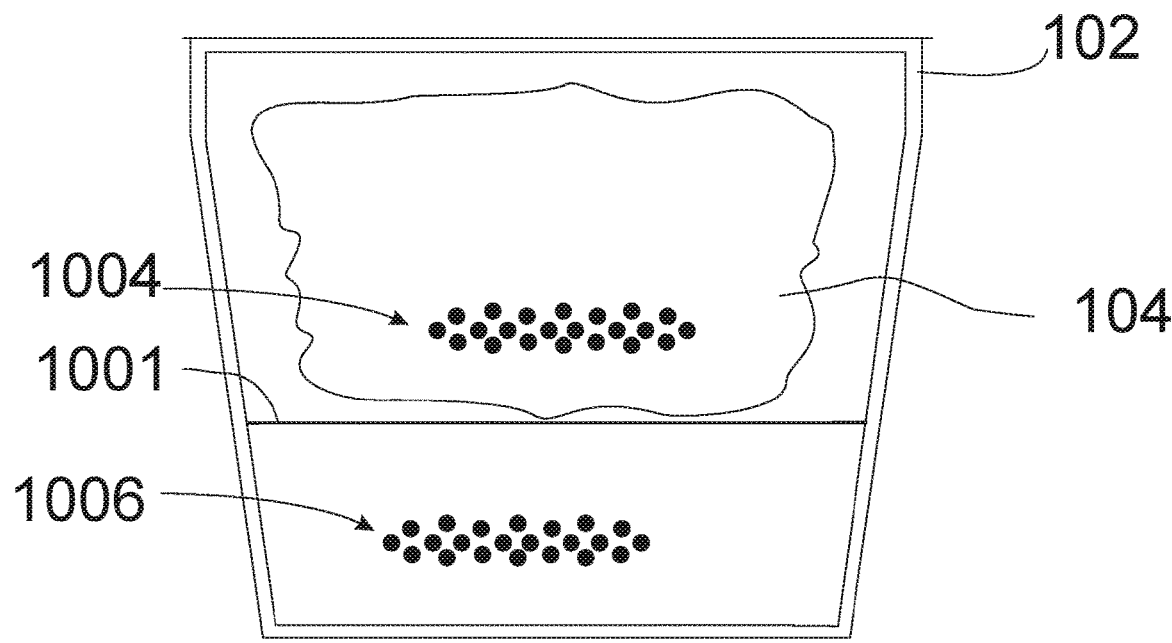
Figure 10B:
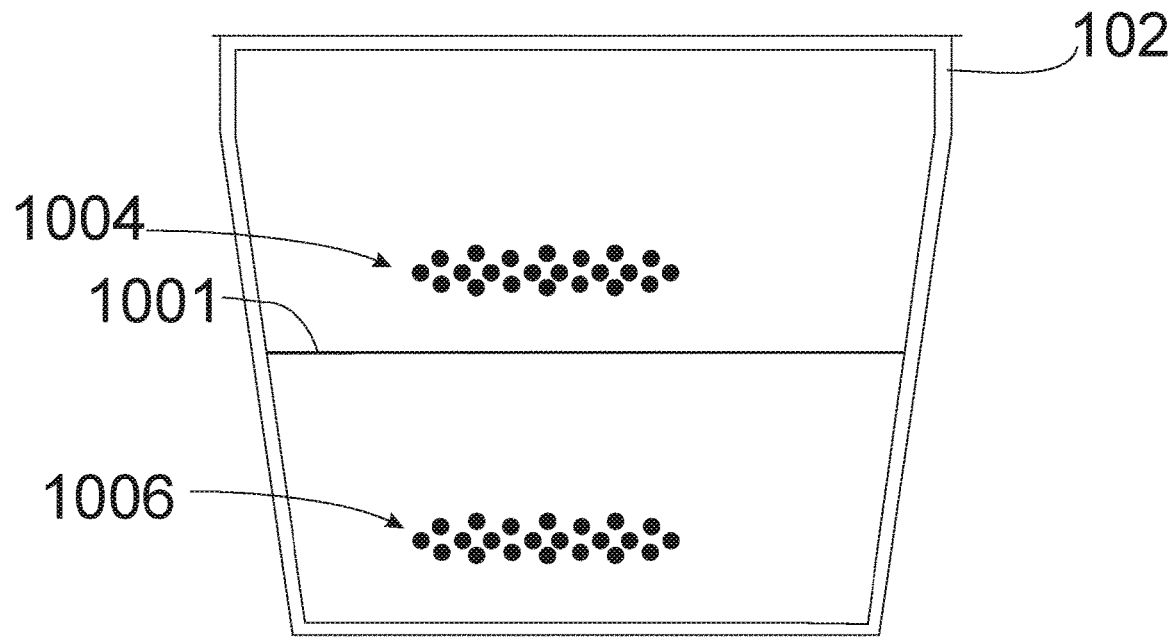
Figure 10C:
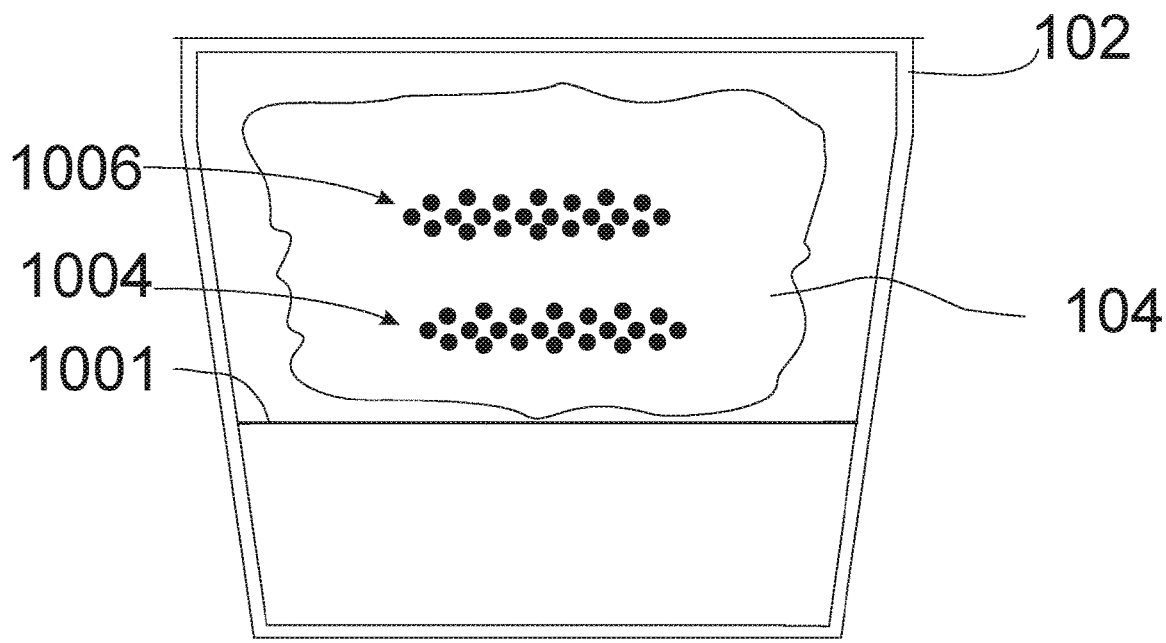
Figure 10D:
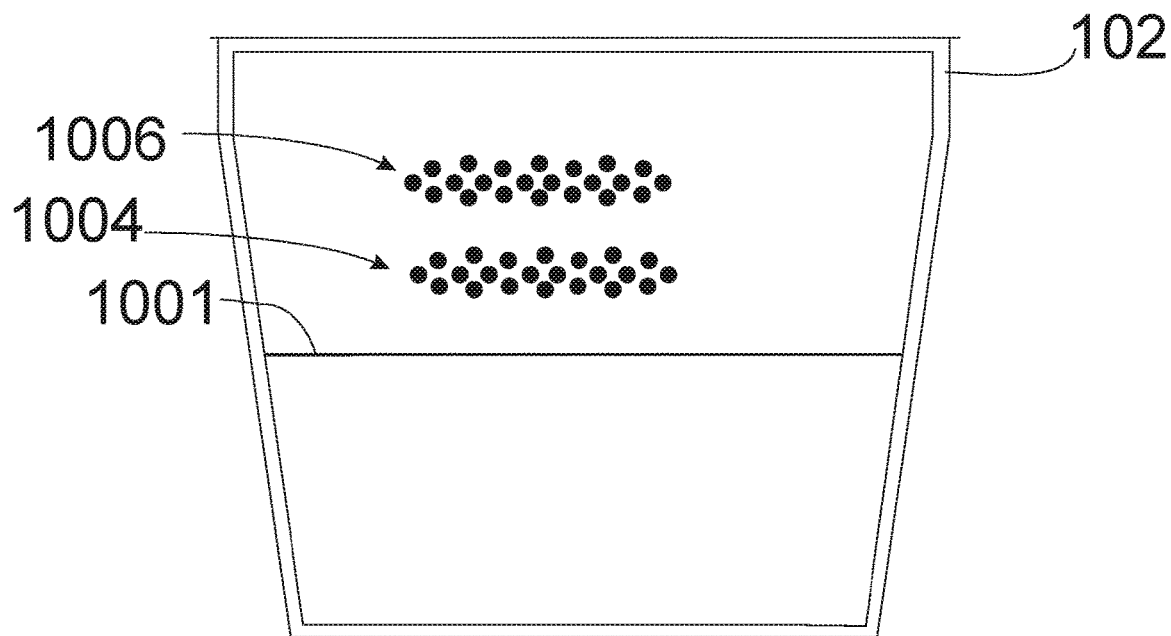

FIGS. 10A-D are sectional views of alternate cannabinoid delivery system illustrating various divider element configurations according embodiments of the present invention. The single use coffee containment system comprises a hollow housing 102 as previously discussed. In these embodiments, a divider element 1001 is provided, wherein the divider element is a screen, such as a mesh filter having a filter size. In one embodiment, in FIG. 10A, a filter 104 contains coffee or tea 1004. In alternative embodiments, the hot chocolate, a beverage mix, etc. may replace or be in addition to the coffee or tea. These items are provided above the divider element. *Cannabis* plant matter 1006 is positioned below the divider element. As previously discussed, during operation (brewing), the housing of the single use coffee containment system is pierced in both the top surface and the bottom surface of the housing while hot pressurized water enters the housing, goes through the filter bag and out the bottom surface into a cup defining a beverage. The hot pressurized water infuses the coffee or tea, the divider retains the filter bag with the coffee or tea in the housing, while the *cannabis* plant matter exits the bottom surface into the cup. In this embodiment, the *cannabis* plant matter may be larger than the filter size of the divider. In the embodiment of FIG. 10B is similar to the embodiment of FIG. 10A, however there is no filter bad, and the coffee or tea is loose above the divider. The embodiments, of FIGS. 10C-D are similar, however in these embodiments, the *cannabis* plant matter is positioned above the divider, and the *cannabis* plant matter is smaller than the filter size (both of the filter bad and divider screen). In some embodiments, the *cannabis* plant matter is initially larger than the *cannabis*, wherein the hot pressurized water dissolves the *cannabis* plant matter to a size smaller than the filter size of both the filter bag and the divider screen. The divider element is configured to match the inner circumference of the housing, such that no particles larger than the divider screen filter size passes through the divider. In situations where just hot chocolate or a beverage mix is provided in place of the coffee or tea, these elements may not be subjected as the same size requirements as coffee or tea, depending on what is desired by the consumer. For instance, the consumer does not want to drink ground coffee beans or tea leaves, but powdered chocolate or a beverage mix may be acceptable, thus the hot chocolate and/or beverage mix may be smaller than the filter size.

Although the invention has been described in considerable detail in language specific to structural features and or method acts, it is to be understood that the invention defined in the appended claims is not necessarily limited to the specific features or acts described. Rather, the specific features and acts are disclosed as exemplary preferred forms of implementing the claimed invention. Stated otherwise, it is to be understood that the phraseology and terminology employed herein, as well as the abstract, are for the purpose of description and should not be regarded as limiting. Therefore, while exemplary illustrative embodiments of the invention have been described, numerous variations and alternative embodiments will occur to those skilled in the art. Such variations and alternate embodiments are contemplated, and can be made without departing from the spirit and scope of the invention. For example, in one embodiment, the filter size of the standard coffee filter or coffee filter bag is increased greater than the typical 20 microns allowing the ground *cannabis* plant matter to easily escape the filter. In other embodiments, the standard coffee filter, coffee filter bag, or ground coffee, is infused, saturated, soaked, coated, or sprayed with cannabinoids such that the beverage would be infused with the cannabinoids during the brewing process. In some embodiments, the cannabinoid delivery system may be provided outside the portafilter for espresso coffee machines or other coffee machines, wherein the cannabinoid delivery system may be in any location that the hot water comes in contact with. Yet in other embodiments, although a single-use system is taught and discussed, the present invention may be modified to be reusable. That is, the *cannabis* delivery system is configured to be reused after brewing.

What is claimed is:

1. A single use cannabinoid delivery system comprising: a hollow housing holding a filter bag comprising *cannabis* plant matter particles and ground coffee or tea, wherein the filter bag is constructed of mesh having a plurality of openings, and the *cannabis* plant matter particles are smaller than the plurality of openings.

2. The system of claim 1, wherein the single use cannabinoid delivery system is configured to be used with a single-serve brewing machine.

3. The system of claim 2, wherein the single-serve brewing machine is configured to enable hot water to pass through the single use cannabinoid delivery system to extract the ground coffee, tea and dispense the *cannabis* plant matter particles into the hot water which is configured to be collected into a cup defining a beverage.

4. The system of claim 1, wherein the *cannabis* plant matter particles are encapsulated nanoparticles.

5. The system of claim 1, wherein the *cannabis* plant matter particles are configured to be water soluble.

6. The system of claim 1, wherein the ground coffee or tea is saturated in the *cannabis* plant matter particles.

* * * * *